United States Patent [19]
Ashjian et al.

[11] Patent Number: 5,691,281
[45] Date of Patent: Nov. 25, 1997

[54] WELL FLUIDS BASED ON LOW VISCOSITY SYNTHETIC HYDROCARBONS

[75] Inventors: Henry Ashjian, E. Brunswick, N.J.; Suzzy C. Ho, Dayton, Ohio; Margaret M. Wu, Skillman, N.J.

[73] Assignee: Mobil Oil Corporation, Fairfax, Va.

[21] Appl. No.: 321,006

[22] Filed: Oct. 6, 1994

[51] Int. Cl.$^6$ .................... C09K 7/02; C09K 7/06
[52] U.S. Cl. ........................... 507/103; 507/203
[58] Field of Search ................ 507/103, 905, 507/203

[56] References Cited

U.S. PATENT DOCUMENTS

| | | | |
|---|---|---|---|
| H1000 | 12/1991 | Patel et al. | 507/103 |
| 4,108,889 | 8/1978 | Connor | 585/664 |
| 4,787,990 | 11/1988 | Boyd | 252/8.511 |
| 5,096,883 | 3/1992 | Mercer et al. | 507/103 |
| 5,189,012 | 2/1993 | Patel et al. | 507/103 |
| 5,432,152 | 7/1995 | Dawson et al. | 507/103 |
| 5,589,442 | 12/1996 | Gee et al. | 507/103 |
| 5,605,879 | 2/1997 | Halliday et al. | 507/103 |

FOREIGN PATENT DOCUMENTS 325466  1/1989  European Pat. Off. .

OTHER PUBLICATIONS

S. Dewell, "The Ultidrill System" brochure, (1994).

*Primary Examiner*—Philip Tucker
*Attorney, Agent, or Firm*—Dennis P. Santini; Lori F. Cuomo

[57] ABSTRACT

Solid, waxy 1-olefins may be converted to low viscosity liquid products by carrying out a double bond isomerization in the presence of a solid acidic catalyst such as an acidic clay or a zeolite under mild conditions. The olefin isomer products are useful in the formulation of well fluids such as drilling muds, especially useful in offshore drilling. The preferred oils for making up the well fluids are formulated with a hydrocarbon oil blend of the low viscosity olefin isomer together with a $C_{12}$ to $C_{18}$ paraffinic hydrocarbon of petroleum origin and a $C_{10}$ to $C_{32}$ olefin such as tetradecene-1. The fluids exhibit good biodegradability and are non-toxic to marine organisms; they also meet viscosity and pour points specifications for formulation into oil based muds.

23 Claims, No Drawings

WELL FLUIDS BASED ON LOW VISCOSITY SYNTHETIC HYDROCARBONS

FIELD OF THE INVENTION

The present invention relates to a novel group of synthetic hydrocarbons and to well fluids based on them, especially to drilling fluids or muds which are useful in the rotary drilling process used for making wells into subterranean formations containing oil, gas or other minerals.

BACKGROUND OF THE INVENTION

The rotary drilling process is used for making wells for the production of oil, gas and other subterranean minerals such as sulfur. In rotary drilling operations, a drill bit at the end of a drill string is used to penetrate the subterranean formations. This drill bit may be driven by a rotating drill string or a drill motor powered, for example, by hydraulic power. During the rotary drilling operation, a fluid, conventionally referred to as drilling mud, is circulated from the drilling equipment of the surface down to the drill bit where it escapes around the drill bit and returns to the surface along the annular space between the drill bit and the surrounding subsurface formations. The drilling mud lubricates the downhole equipment and brings the formation cuttings to the surface where they can be separated from the mud before it is recirculated. In addition, the drilling mud serves to counterbalance formation pressures and may also form a cake around the walls of the borehole to seal the formations. The lubricating action of the drilling mud is particularly important with the conventional rotating drill string since it provides a lubricant or cushion between the rotating drill pipe and the walls of the borehole, helping to prevent sticking of the drill string in the hole. The characteristics and performance of drilling muds are described, for example, in Kirk-Othmer, Encyclopedia of Chemical Technology, Third Edition, John Wiley and Sons, 1982, under Petroleum (Drilling Muds), to which reference is made for a description of drilling muds and the materials used in formulating them.

Drilling muds are usually classified as either water-based muds or oil-based muds, depending upon the character of the continuous phase of the mud, although water-based muds may contain oil and oil-based muds may contain water. Water-based muds conventionally comprise a hydratable clay, usually of the montmorillonite family, suspended in water with the aid of suitable surfactants, emulsifiers and other additives including salts, pH control agents and weighting agents such as barite. The water makes up the continuous phase of the mud and is usually present in an amount of at least 50 percent of the entire composition; oil may be present in minor amounts but will typically not exceed the amount of the water so that the mud will retain its character as a water-continuous phase material. Oil-based muds on the other hand, generally use a hydrocarbon oil as the main liquid component with other materials such as clays or colloidal asphalts added to provide the desired viscosity together with emulsifiers, gellants and other additives including weighting agents. Water may be present in greater or lesser amounts but will usually not be greater than 50 percent of the entire composition; if more than about 10 percent water is present, the mud is often referred to as an invert emulsion, i.e a water-in-oil emulsion. In invert emulsion fluids, the amount of water is typically up to about 40 weight percent with the oil and the additives making up the remainder of the fluid.

Oil-based muds are conventionally formulated with diesel oil or kerosene as the main oil component as these hydrocarbon fractions generally posses the requisite viscosity characteristics. They do, however, posses the disadvantage of being relatively toxic to marine life and the discharge of drilling muds containing these oils into marine waters is usually strictly controlled because of the serious effects which the oil components may have on marine organisms, particularly those which are commercially important for food. For this reason, offshore drilling rigs must return oil-based muds to shore after they have been used whereas water-based muds may generally be discharged into the ocean without any deleterious effects.

Oil-based muds may be made environmentally acceptable by the use of oils which posses low inherent toxicity to marine organisms and good biodegradability. These properties are associated in hydrocarbons with low aromaticity. For these reasons, drilling fluids based on linear paraffins might be considered desirable. On the other hand, however, the linear paraffins tend to have high pour points and the higher molecular weight fractions tend to be waxy so that in the low temperature environments frequently encountered in offshore drilling, there is a significant risk that waxy paraffin deposits will be formed in the downhole equipment or in the riser connecting the sea bed to the drilling equipment. In either event, this is unacceptable so that highly paraffinic oils have not achieved any significant utility as the base fluids in oil based muds.

U.S. Pat. No. 4,787,990 (Boyd) discloses a low toxicity oil for use in oil- and water-based drilling fluids. The low toxicity of the oil coupled with lack of water sheen as well as the non-fluorescence characteristics which assist in the monitoring of the drill cuttings, are stated to make the muds useful in offshore drilling operations. The oil has a very limited aromatic content (less than 0.5 percent) and a low n-paraffin content (less than 1 percent) in order to confer the desired mud characteristics.

EP 325466 (Trahan/Coastal Mud Inc.) proposes the use of synthetic hydrocarbon fluid in water-based drilling muds and spotting fluids. The synthetic hydrocarbons are poly (alpha-olefins) (PAOs) which are predominantly iso-paraffinic hydrocarbons with no aromatic content. They are produced by the oligomerization of alpha olefins such as 1-decene with the oligomerization product being hydrogenated to reduce residual unsaturation. The oligomers are predominantly dimer, trimer, tetramer and pentamer in order to achieve the desired viscosity of approximately 2 cS (100° C.). In the oligomerization process, the olefin monomer is oligomerized using a homogeneous phase, Lewis acid catalyst such as aluminum trichloride or boron trifluoride. When the oligomerization has proceeded to the desired degree with the PAO product having the requisite viscosity, the catalyst is separated and the initial oligomerization product subjected to hydrogenation, usually over a nickel catalyst, for example, nickel on kieselguhr. A residual monomer content below 0.5% is stated to be desirable. Although the well fluids described in the Trahan application are stated to possess low toxicity, the use of PAOs, which are synthetic materials and therefore relatively costly, is not favorable from the economic point of view. The incentive to develop a drilling mud based on conventional petroleum-based oils therefore remains.

U.S. Pat. No. 5,189,012 (Patel) describes drilling fluids based on oil phase continuous emulsions in which the oil phase consists entirely of a PAO. While such emulsions may possess good properties as described here, the PAOs, being synthetic materials are rather higher in cost than conventional mineral oil based emulsions and currently, the supply of PAO type materials and their precursors is limited. It would therefore be desirable to find an alternative for PAO type materials for use in formulating well fluids.

U.S. patent application Ser. No. 08/128,186, filed Sep. 29, 1993 (Mobil Case 7178) describes well fluids of improved biodegradability and low marine toxicity which are formulated partly from PAOs as well as other components including paraffins and olefins. Although well fluids of the type described in this application perform well, they still contain a certain amount of PAO for which a replacement would be desirable.

SUMMARY OF THE INVENTION

We have now found a class of novel synthetic hydrocarbons which have low levels of marine toxicity, exhibit good inherent biodegradability and which can be made from precursors which are in good supply at the present time. These synthetic hydrocarbons also possess other interesting properties which make them suitable for other uses including automotive and industrial lubricants including engine oils. Well fluids can be formulated with these synthetic hydrocarbons to possess the same low toxicity and biodegradability characteristics as the hydrocarbons themselves as well as good viscometric properties including low pour point.

According to the present invention, these synthetic hydrocarbons are made by the isomerization of a long chain 1-olefin containing at least 18 carbon atoms, normally from 20 to 50, usually 20 to 30, carbon atoms. The isomerization, which is conducted under mild conditions in the presence of a solid heterogeneous catalyst such as an acidic clay or a zeolite, produces a rearrangement of the molecular structure of the olefin by double bond isomerization, i.e. shift of the double bond, which converts these characteristically high melting products, usually solid at room temperature, to liquids of low viscosity and low pour point. Although the desired isomerization is frequently accompanied by a minor degree of olefin oligomerization resulting in an increase in product viscosity, this is usually limited in extent depending on the type of catalyst used and does not adversely affect the utility of the isomer product for formulating well fluids.

Well fluids, including drilling muds, spotting fluids and other products for the treatment of subterranean wells may be formulated with the novel synthetic hydrocarbons, either as the sole hydrocarbon fluid or, alternatively, with other hydrocarbons in order to obtain the desired product viscosmetrics. A preferred class of well fluids are formulated in the manner described in application Ser. No. 08/128,186 but with the present olefin isomer product replacing the PAO component of the earlier application.

The blended well fluids may be formulated with a mixed mineral oil olefinic-paraffinic hydrocarbon component containing from 10 to 32 carbon atoms in addition to the olefin isomer product to give a blend of the correct viscometrics. With the olefin isomer component present, the hydrocarbon oil has a viscosity of 1 to 4 cS at 100° C. (ASTM D-445), a flash point of at least 70° C., and a pour point no higher than +5° C. These well fluids have been found to have good biodegradability and low marine toxicity.

DETAILED DESCRIPTION OF THE INVENTION

Hydrocarbon Synthesis

According to the present invention, long chain waxy olefins which are solid at room temperature and which contain at least 18 and usually at least 20 carbon atoms, are subjected to double bond isomerization by contact with an acidic catalyst to convert the olefin to an isomer product which is liquid at room temperature and which possesses low viscosity and low pour point.

The waxy olefins which are used as the starting material are typically may be obtained as by-products from the production of alpha-olefins, PAOs or from other sources such as Fischer-Tropsch synthesis which also produces these solid, waxy products which can be converted to low viscosity liquids by double bond isomerization. Thes olefins are usually obtained as mixtures of 1-olefins with a range of carbon numbers depending on the process ised for their manufacture. A typical waxy olefin product of this type is a mixture of $C_{20}$ to $C_{24}$ 1-olefins produced as a by-product in the synthesis of alpha-olefins by the ethylene growth reaction. Another waxy olefin of this type is a similar mixture extending from $C_{24}$ to $C_{28}$ and produced in the same way. These materials are solid at room temeperature or just above but, on treatment with the acidic isomerization catalyst, are converted to liquids of low viscosity and low pour point.

The double bond isomerization treatment is carried out under mild conditions in the presence of a solid heterogeneous catalyst so as to minimize the extent of cracking, oligomerization and other undesired side reactions which reduce the yield of the desired low viscosity liquid product. Suitable acidic catalysts which may be used include acid-treated clays which are readily available commercially.

Other solid, acid-acting heterogeneous catalysts which may also be used, are the acid-acting crystalline molecular sieves, especially the zeolites. The zeolites which are particularly useful for the present isomerization reaction are the large pore size zeolites, that is, the zeolites which have a crystalline structure characterized by 12-member rings of oxygen atoms, such as the faujasitic zeolites zeolite X and zeolite Y (in forms including USY, UHP-Y), Linde-L, ZSM-4, mordenite and zeolite beta. These large pore size zeolites normally have a Constraint Index of not more than 2, measured in the manner described in U.S. Pat. No. 4,016,218. Zeolites X and Y, for example, have Constraint Indices of about 0.6 while zeolite beta has a variable Constraint Index which may be from about 0.6 to 2. The zeolites with a three-dimensional structure are preferred over those with a two-dimensional arrangement such as mordenite. The intermediate pore size zeolites such as ZSM-5, ZSM-11, ZSM-12, ZSM-22, ZSM-23, and ZSM-35 also have potential for use in the isomerization reaction reaction because even if their pore sizes impose diffusional constraints on access to their internal pore structures, the surface acidity may be sufficient to catalyze the double bond shift. Certain intermediate pore size zeolites such as MCM-22 which are known to be effective for catalyzing reactions involving relatively large or lengthy molecules have potential for this purpose; see Leonowicz et al. Science, 264, (1994) 1910–1913. The aluminosilicate forms of the zeolites are normally preferred as they have been found to possess the requisite degree of acidity although other large pore size crystalline materials which may be used include the aluminophosphates (ALPOs) and the silicoaluminophosphates (SAPOs) and other related materials of comparable acidic functionality.

The isomerization of the olefin starting material is carried out by contacting the waxy olefin with the catalyst at moderately elevated temperature, typically from about 100° to 400° C. and, in most cases from about 100° to 200° C. with the olefin starting material in the liquid phase. The reaction may be carried out in a simple stirred reaction vessel at atmospheric pressure, although pressure may be applied if desired. Typical reaction duration is from about 3 to 48 hours, usually from about 3 to 24 or 3 to 36 hours. The progress of the isomerization may be ascertained by IR analysis. Product recovery may be by simple removal of the solid catalyst by filtration followed by distillation to remove light ends formed during the reaction.

A certain degree of oligomerization takes place during the reaction as does some cracking, with the formation of oligomers and light ends. The amount of these by-products will depend on the identity of the catalyst as well as on the exact conditions used. Since the objective of the reaction is to form a low viscosity, low pour point, isomerized liquid reaction product, these side reactions should be reduced as much as possible. The extent of oligomer formation may be monitored by measuring the viscosity increase of the mixture. Light ends and oligomers may be separated from the reaction mixture by distillation; if required, any solid starting material or solid by-products may be separated by filtration.

Although the product, being an isomer of the original starting material, is unsaturated, it may be used in well fluids as such without hydrogenation since the residual unsaturation is not normally a source of instability in compositions of this kind which may, in any event, also contain other unsaturated components; hydrogenation may, however, be carried out if the unsaturation is likely to lead to instability in service, for example, as a lubricating or hydraulic fluid in applications where high temperatures may be encountered, although at this will be at the expense of some increase in product viscosity.

The olefin isomer product has a low viscosity which makes it suitable for use where a hydrocarbon fluid with these characteristics is useful, especially in the formulation of well fluids, as described below. Typical product viscosities, after removal of light ends, are from about 4 to about 30 or 40 cS at 40° C. and about 1 to 6 cS at 100° C., indicating high values of viscosity index (VI), typically from about 180 to 200, indicating potential utility as a lubricating or hydraulic fluid. The pour point of the isomerized product is not more than 5° C., usually not more than 0° C., with values from −10° to −20° C. being typical. Other characteristics, including flash point, render these olefin isomer products highly suitable for blending with other components to make well fluids as described below.

Well Fluid Formulation

The olefin isomer reaction products obtained from the process may be used as the sole oil component of well fluids but normally the cost will be too high for this utility. Nevertheless, certain well treatment fluids such as spotting fluids to relieve stuck drill strings may be formulated in this way when cost is less of a consideration but biodegradability and low toxicity are important factors. Well fluids formulated with the present olefin isomer products may be made up using the products in the same way as other oils, for example, as described in U.S. Pat. Nos. 4,787,990 (Boyd) or 5,189,012 (Patel) or EP 325466 (Trahan/Coastal Mud Inc.), to which reference is made for a description of such well fluids and their preparation. Thus, in addition to the olefin isomer component, the finished well fluids will contain a clay component, usually of the montmorillonite family, together suitable surfactants, emulsifiers and other additives including salts, pH control agents and weighting agents such as barite and other conventional drilling fluid materials.

The oil component of well fluids normally has a viscosity of 1 to 4 cS at 100° C. (ASTM D-445) and in most cases should be not more than 2 cS. The flash point (ASTM D-93) should be at least 70° C., preferably at least 100° C. or higher, for example, at least 120° C. Pour point (ASTM D-97) should be no higher than +5° C., preferably no higher than 0° or even −5° C. The specific gravity of the oil is in the range 0.75 to 0.82. at 60° F. (15.6° C.)(ASTM D-1298). Although the olefin isomer product will not normally meet all these requirements, it can be blended with other fluids, especially other hydrocarbons, to meet the desired viscometrics and other specifications, e.g. flash point.

A preferred blend is similar to that described in U.S. patent application Ser. No. 08/128,186, filed 29, Sep., 1993 (Mobil Case 7178), except that the PAO component of Ser. No. 08/128,186 is replaced by the olefin isomer product of the present invention. Reference is made to Ser. No. 08/128, 186 for a complete description of such well fluids and their preparation. Well fluids of this type may be formulated with an oil component which is a hydrocarbon blend of a mixed petroleum-based (mineral oil origin) paraffinic-olefinic component and the low viscosity olefin isomer component, together with the other fluid components mentioned above. The viscometrics of the oil component will be as described above. In these hydrocarbon blends, the olefin isomer is normally used in an amount from 5 to 80 weight percent, typically from 5 to 40, preferably from 10 to 30, weight percent of the total hydrocarbons in the oil component of the mud.

Although various combinations of hydrocarbons and other materials such as esters may be used, blends of the olefin isomers with (i) a light paraffinic oil with essentially no aromatic content and (ii) an olefin component, will normally give good blend viscometrics, flash point, bioacceptability as well as favorable product economics. In blends of this type, the mineral oil component is a mixture of $C_{10}$–$C_{18}$ n-paraffins and $C_{10}$–$C_{32}$ olefins of low viscosity suitable for formulation into the well fluids after the addition of the olefin isomer component.

The paraffin component will normally be used to maintain the viscosity of the blend at the desired low value of not more than 2 cS (100° C.). Because many of the low viscosity paraffins tend to increase the pour points of the blends, especially with longer paraffin chain lengths, they normally need to be used in conjunction with the low pour point olefins for good low temperature properties. Preferred paraffinic hydrocarbons which can be used to make up the major part of the hydrocarbon blend are $C_{10}$–$C_{18}$ paraffins, usually n-paraffins although minor amounts of iso-paraffins and cycloparaffins may be present as impurities. The use of paraffins containing large amounts of $C_{12}$— material will not normally be favored because of the lower flash points associated with these light ends. Hydrogenated olefins such as hydrogenated tetradecene may be used. Mixtures of paraffins may also be used such as those described below in order to procure the desired combination of properties. The preferred paraffinic mixtures typically contain at least 98 weight percent n-paraffins and are essentially free of aromatics (less than 1 and preferably less than 0.5, weight percent monocyclic aromatics). The paraffinic component need not include paraffins across the entire $C_{10}$–$C_{18}$ range but may be more limited in terms of carbon number in order to provide the desired viscometrics. Typical paraffinic mixtures for blending with the olefinic component and the olefin isomer are shown in Table 1 below. One is a $C_{10}$–$C_{13}$ mixture with a low viscosity, pour point and flash point while the other two are higher carbon number ($C_{12}$–$C_{14}$, $C_{14}$–$C_{18}$) mixtures with correspondingly higher pour points, flash points and viscosities. Paraffinic mixtures such as these may be used either as such or as blends with each other to achieve the desired properties in the final hydrocarbon blend. The amount of the paraffin component will normally be in the range of about 50 to 90 weight percent of the blend, and in most cases in the range of about 60 to 85 weight percent.

Properties of typical hydrogenated olefin dimers which may be used in the present blends are given in Table 2 below, with the properties of tetradecene-1 (olefin) given for comparison.

TABLE 2

| | | | Hydrogenated Olefin Dimer properties | | | | | |
|---|---|---|---|---|---|---|---|---|
| Olefin C number | $C14^=$ 14 | $C_8$ Dimer 16 | $C_8/C_{10}/C_{12}$ Dimer 16,18,20,22,24 | $C_{10}$ Dimer 20 | $C_{10}/C_{12}$ Dimer 20,22,24 | $C_{12}$ Dimer 24 | $C_{14}$ Dimer 28 | $C_{16}$ Dimer 32 |
| Product Properties | | | | | | | | |
| KV, 40° C., cS | 1.87 | 2.36 | 8.40 | 5.00 | 6.44 | 10.30 | 15.00 | 18.80 |
| KV, 100° C., cS | 0.86 | 1.09 | 2.42 | 1.70 | 2.02 | 2.80 | 3.60 | 4.40 |
| Pour Pt., °C. | −12 | <−63 | <−63 | <−63 | <−63 | −60 | −36 | −12 |
| Flash Pt., °C. | 107 | 122 | 122 | 150 | 150 | 175 | 203 | 220 |

TABLE 1

| | Paraffin Hydrocarbon Blends | | | |
|---|---|---|---|---|
| Physical Properties | ASTM | Paraffin A | Paraffin B | Paraffin C |
| Viscosity @ | | | | |
| 38° C. | D-445 | 1.37 | 1.93 | 2.42 |
| 25° C. | D-445 | 1.68 | 2.41 | 3.27 |
| Pour Point °C. | D-97 | −21 | −4 | 7 |
| Spec. Gravity @ | D-1298 | 0.751 | 0.764 | 0.771 |
| Flash Point °C. | D-93 | 69 | 93 | 118 |
| Composition, mass % | Mass | 98.1 | 98.7 | 99.4 |
| Normal Alkanes | spec | | | |
| C10 | | 13 | — | — |
| C11 | | 36 | — | — |
| C12 | | 44 | 12 | — |
| C13 | | 7 | 60 | — |
| C14 | | — | 28 | 32–34 |
| C15 | | — | — | 42–45 |
| C16 | | — | — | 16–18 |
| C17 | | — | — | 4–6 |
| C18 | | — | — | 1–3 |
| Isoparaffins | | 0.2 | 0.6 | 0.6 |
| Cycloparaffins | | 1.1 | 0.6 | 0.6 |
| Mono-Aromatics | U.V. | 0.6 | 0.2 | 0.01 |

Another group of paraffinic liquids which may be used for blending with the olefin isomers are the hydrogenated olefin dimers containing from 16 to 32 carbon atoms. These paraffins, which are obtained by the hydrogenation of dimers of $C_8$–$C_{16}$ olefins, are characterized by a desirable combination of low viscosity coupled with low pour point and high flash point.

The viscosity of these hydrogenated dimers is below 3 cS (100° C.) for carbon numbers up to C24 and is below 5 cS (100° C.) at $C_{32}$. The pour points of these hydrogenated dimers is markedly lower than that of the straight chain paraffins, being no higher than −60° C. with carbon numbers up to $C_{24}$ and no higher than −12° C. at $C_{32}$. Flash points are at least 120° C. in all cases, making these materials highly useful for the present purposes. The olefin dimers are conveniently obtainable by the dimerization of shorter olefins such as octene, decene, dodecene, tetradecene, hexadecene, or mixtures of these, using a cationic catalyst such as boron trifluoride. Blends of hydrogenated olefins may be used to obtain the desired viscometrics, particularly blends of tetradecane with other hydrogenated olefins.

An olefinic component, which is normally present to ensure a suitably low pour point for the blend, is normally a $C_{12}$–$C_{32}$ olefin. Olefins which may be used for this purpose include alpha-olefins such as 1-dodecene or 1-tetradecene, as well as higher olefins up to about triacosene. The lower olefins, especially tetradecene, hexadecene and decene dimer ($C_{20}$) may normally be used on their own without the addition of the paraffinic component as they have a sufficiently low viscosity as well as low pour point; the higher olefins containing $C_{20}+$ components will, however, normally require the addition of the paraffinic component to ensure that the blend viscosity is not more than the required 2 cS (100° C.). The use of olefins containing large amounts of $C_{12}$— material will not normally be favored because of the lower flash points associated with these light ends. A convenient source of the higher olefins above about hexadecene ($C_{16}$–$C_{32}$) is the olefin dimers mentioned above which are produced by the dimerization of shorter olefins such as octene, decene, dodecene, tetradecene or hexadecene, using a cationic catalyst such as boron trifluoride. These olefin dimers have the potential for producing blends of even more favorable pour point than the blends with the hydrogenated dimers. Blends of olefins may be used to obtain the desired viscometrics, particularly blends of tetradecene with other olefins. The amount of the olefin in the hydrocarbon blend is usually in the range of 5 to 80 weight percent and in most cases, from 10 to 50 weight percent of the blend. Normally, from 15 to about 30–40 weight percent of the olefin component will be preferred.

The oil component is formulated into drilling muds or other well treatment fluids such as completion fluids. Formulation will, with the exception of the choice of the specific oil component as the hydrocarbon base fluid, be conventional in type and normal types of additives including emulsifiers, surfactants, viscosity-modifying agents, weighting agents and other components will be suitable. The density of the muds will typically be in the normal range of about 6 to 28 pounds per gallon.

The preferred type of muds using the present oil blends are oil-based muds, especially the invert-emulsion type muds which contain water dispersed in the oil component which makes up the contiuous phase of the final emulsion-type mud. In muds of the invert emulsion type, the amount of oil in the final mud will typically be from about 25 to 75% by weight, and is typically in the range of 40 to 60% by weight of the final mud. The balance of the mud typically comprises water and the normal additives such as clays, salts such as sodium chloride, calcium chloride or calcium bromide, weighting agents such as barite or hematite (high density fluids) or dolomite or calcite (low density fluids such as completion and work-over fluids), viscosity modifiers, pH control agents, circulation control agents such as ground seed hulls or shredded cellulosic materials and other additives wehich may be conventional in type. When the oil component is formulated into the mud, conventional blending procedures are used, for example, blending the oil with the emulsifiers and surfactants, followed by mixing with water in the requisite amounts to form the final invert (water-in-oil) emulsion which may then be blended with other additives, as necessary. If the oil component is used in water-based muds, it would appropriately be used in an amount of up to about 50 weight percent of the mud with the other components being water and conventional type additives, as described above.

The well fluids based on these paraffin/olefin/olefin isomer blends may be used as drilling muds in rotary drilling as well as in other well operations, for example, for filling the well during testing, completion work-over, in the same way as other muds and well treatment fluids. the fluids based on the present oils have, however, the particular advantage that in offshore drilling operations, cuttings contaminated with the fluids may be disposed of by discharge into the sea. The good biodegradability and non-toxicity of the present muds permits this type of cuttings disposal in the ocean environment without any significant risk of persistent pollution.

EXAMPLES

The folowing Examples illustrate the synthesis of the olefin isomer products.

Examples 1–10

Preparation of Olefin Isomer

The 1-olefin used as the starting material was a $C_{20}$–$C_{24}$ 1-olefin mixture available from Chevron as Gulftene 2024™. This material is solid at room temperature (m.p. 35.6° C.) and has a viscosity of 2.1 cS at 100° C. 200 g. of this material was mixed with 10 g. of a calcined acidic clay, Filtrol™ Clay Grade 22 (available from Harshaw-Filtrol (Engelhard) Co.) and heated to 150° C. for 24 hours. The catalyst was removed by filtration at 60° C. The product was a low viscosity liquid and was obtained in a yield of 97 percent. The reaction conditions and product properties are shown in Table 3 below.

For Examples 2–10, the preparation was repeated using different catalysts and conditions, with the results shown in Table 3 below. The results show that oligomerization takes place together with the isomerization, with this effect being more marked with the clay catalysts than with the zeolites (zeolite beta or MCM-22). With the zeolite catalysts, the major reaction was double bond isomerization, only a very small degree of oligomerization taking place at low catalyst concentrations (Example 8). In all cases the isomerization reaction converted the solid 1-olefin starting material into a low viscosity liquid.

The biodegradability of the product of Example 2 was found to be 63% in the EPA Shaker Flask Test, as compared to 49% for a conventional 2 cS PAO.

Examples 11–14

These Examples used a different waxy olefin starting material, a $C_{24}$–$C_{28}$ olefin mixture available from Chevron as Gulftene 2428™, which is a hard solid at room temperature (m.p. 52.2° C.) with a viscosity of 2.5 cS at 100° C. The reaction conditions and product properties are shown in Table 4 below. With the higher melting staring material, higher temperature refluxing is required to convert to a liquid product.

TABLE 3

Isomerization of $C_{20}$–$C_{24}$ 1-Olefins

| Example No. | 1 | 2 | 3 | 4 | 5 | 6 | 7 | 8 | 9 | 10 |
|---|---|---|---|---|---|---|---|---|---|---|
| Run No. | C1963-163C | ME130 | ME135 | ME137 | ME138 | ME139 | ME140 | ME141 | ME142 | ME144 |
| Catalyst Type | Filtrol 22 | Filtrol 22 | Filtrol 24 | Filtrol 24 | Beta | Beta | Beta | MCM-22 | MCM-22 | Beta |
| Catalyst, wt % | 5 | 5 | 3.3 | 3.3 | 1 | 0.3 | 0.1 | 0.3 | 0.1 | 1 |
| Temp., °C. | 150° C. | 175° C. | 175 | 160 | 160 | 180 | 180 | 160 | 180 | 300 |
| Time, hrs | 24 | 24 | 24 | 24 | 24 | 24 | 24 | 24 | 24 | |
| Product Properties | | | | | | | | | | |
| V 100° C., cS | 4.89 | 5.67 | 5.08 | 3.00 | 2.35 | 2.19 | 2.15 | 2.73 | 2.87 | 3.21 |
| V 40° C., cS | 19.27 | 24.92 | 21.49 | 9.77 | 6.82 | 6.28 | 6.06 | 8.77 | 9.10 | 12.2 |
| VI | 194 | 180 | 177 | 180 | 190 | 182 | 189 | 169 | 185 | 131 |
| Pour Pt., °C. | +23 | 16.5 | +11 | 15 | 12 | 13.5 | 23.3 | 13.6 | 10.9 | −2 |
| Product Appearance | sl. cloudy | clear, sl. color | clear, sl color | clear, sl ppt | colorless, no α-vinyl by IR | colorless, no α-vinyl by IR | cloudy, colorless α-vinyl by ir | clear, colorless | clear, sl. yellow | |
| Product Distribution, wt % | | | | | | | | | | |
| C20–C30 | not done | 28.1 | 32.2 | 52.9 | 78.5 | — | 99.4 | 74.9 | 68 | |
| oligomers | — | 71.9 | 67.8 | 47.1 | 21.5 | — | 0.6 | 25.1 | 32.0 | |
| C20-lights | — | 0 | 0 | 0 | 0 | — | 0 | 0 | 0 | |

TABLE 4

Isomerization of $C_{24}$–$C_{28}$ 1-Olefins Over Acidic Catalysts

| Example No. | 11 | 12 | 13 | 14 |
|---|---|---|---|---|
| Run No. | ME136 | ME143 | ME144 | ME145 |
| Catalyst Type | Filtrol 24 | Beta | Beta | Beta |
| Catalyst, wt % | 3.3 | 1 | 1 | 1 |
| Temperature, °C. | 175 | 250 | 300 | 275 |
| Time, hrs. | 24 | 24 | 24 | 24 (300 psi) |
| Product Properties | | | | |
| V100° C., cS | 6.63 | 3.54 | 3.21 | 3.00 |
| V40° C., cS | cannot measure | 14.27 | 12.26 | 11.08 |
| VI | cannot measure | 132 | 131 | 130 |
| Pour point | — | −13 | −1.9 | −28 |
| Product Appearance | solid, no α-vinyl by IR | lt. yellow, cloudy | orange ppt, loss 50% sample by cracking | orange |
| Product Distribution, wt % | | | | |
| C20–C30 | 50.1 | 88.9 | 91.7 | — |
| oligomers | 49.9 | 88.9 | 91.7 | — |
| C20-lights | 0 | 11.1 | 6.3 | — |

Examples 15–19

These Examples illustrate the blending of the olefin isomer product with the paraffinic hydrocarbon and the olefin to make up the oil blend useful in well fluids.

In these Examples, the paraffinic oil component was either a $C_{12}$–$C_{14}$ paraffinic hydrocarbon oil (Paraffin-B above) or a $C_{14}$–$C_{18}$ paraffinic hydrocarbon oil (Paraffin-C above); the olefin component was technical 1-tetradecene (99.6 percent 1-olefins, 95.5 percent $C_{14}$, 2.5 percent $C_{16}$). These components were blended with the olefin isomers prepared in Examples 1, 2, 5 and 6 to make oils suitable for formulation into well fluids. The properties of the blends and comparisons with other blends, including a reference blend made without the olefin isomer, are shown in Table 5 below.

TABLE 5

Olefin Isomer Blends

| Example No. | Ref. | 15 | 16 | 17 | 18 | 19 |
|---|---|---|---|---|---|---|
| Component | | | | | | |
| Ex. 1 Isomer | | 20.0 | 20.0 | | | |
| Ex. 2 Isomer | | | | 18.5 | | |
| Ex. 5 Isomer | | | | | 33.7 | |
| Ex. 6 Isomer | | | | | | 36.1 |
| Paraffin B | | 60.0 | 80.0 | 81.5 | 66.3 | 63.9 |
| Paraffin C | 60.0 | | | | | |
| 1-$C_{14}$= | 20.0 | 20.0 | | | | |
| $C_{10}$ Dimer | 20.0 | | | | | |
| Product Properties | | | | | | |
| KV 40° C., CS | 2.59 | 2.66 | 2.67 | 2.60 | 2.66 | 2.71 |
| KV, 100° C., cS | 1.13 | 1.18 | 1.17 | 1.16 | 1.18 | 1.20 |
| Pour P., °C. | 6 | −3 | 0 | −3 | −6 | −6 |
| Flash Pt., °C. | 124 | 109 | — | — | — | — |

Examples 20–27

Blend simulations were made to determine the expected viscometrics of oil blends containing the olefin isomers of Examples 1, 2, 5 and 6 with paraffins and olefins.

In these Examples, the paraffinic oil component was taken to be Paraffin-B above alone or in combinatiuon with a hydrogenated $C_{20}$ dimer of 1-decene having the properties set out in the table of hydrogenated olefins above (Table 2); the olefin component, when present, was taken to be technical 1-tetradecene (99.6 percent 1-olefins, 95.5 percent $C_{14}$, 2.5 percent $C_{16}$). The blend viscometrics were calculated and are shown in Table 6 below. The results in the table show that it is possible to formulate oils having appropriate viscometrics and flash point suitable for use in drilling fluids using blends of the olefin isomers with paraffins and/or olefins of varying molecular weight, meeting the viscosity specification of 2 cS max. (100° C.), pour point of not more than +3° C. or lower and flash point of at least 100° C.

TABLE 6

Olefin Isomer Blend Simulations

| Example No. | 20 | 21 | 22 | 23 | 24 | 25 | 26 | 27 |
|---|---|---|---|---|---|---|---|---|
| Component | | | | | | | | |
| Ex. 1 Isomer | 10 | 15 | | | | | | |
| Ex. 2 Isomer | | | 10 | 15 | | | | |
| Ex. 5 Isomer | | | | | 10 | 15 | | |
| Ex. 6 Isomer | | | | | | | 10 | 15 |
| Paraffin B | | 75 | | 75 | | 75 | | 75 |
| Hydrogenated $C_{10}$=Dimer | 10 | 10 | 10 | 10 | 10 | 10 | 10 | 10 |
| 1-$C_{14}$= | 80 | | 80 | | 80 | | 80 | |
| Product Properties | | | | | | | | |
| KV 40° C., cS | 2.36 | 2.56 | 2.42 | 2.66 | 2.12 | 1.02 | 2.01 | 2.16 |
| KV 100° C., cS | 1.10 | 1.14 | 1.11 | 1.17 | 1.02 | 2.19 | 1.01 | 1.01 |
| Pour Pt., °C. | −14 | −7 | −14 | −8 | −15 | −9 | −14 | −9 |
| Flash Pt., °C. | 117 | 109 | 117 | 109 | 117 | 109 | 117 | 109 |

We claim:

1. A well fluid which comprises a hydrocarbon oil comprising:
    (i) a liquid olefin isomer component produced by the double bond isomerization of a waxy $C_{20}$+ 1-olefin, and
    (ii) a low viscosity hydrocarbon which comprises an n-paraffin hydrocarbon component of petroleum origin in the $C_{10}$–$C_{32}$ range, and an olefinic hydrocarbon component in the $C_{10}$–$C_{32}$ range, the oil having the following properties:
    Viscosity at 100° C. 0.5 to 4 cS
    Viscosity at 40° C. 1.0 to 30 cS
    Pour point not above +5° C.
    Flash point not less than 70° C.

2. A well fluid according to claim 1 in which the oil component has the following properties:
    Viscosity at 100° C. 0.7 to 2 cS
    Viscosity at 40° C. 2.0 to 20 cS
    Pour point not above 0° C. Flash point not less than 100° C.

3. A well fluid according to claim 1 in which the oil component has a flash point of at least 100° C.

4. A well fluid according to claim 1 in which the oil component has a pour point from −20° to +5° C.

5. A well fluid according to claim 1 in which the oil component has a pour point from −10° to 0° C.

6. A well fluid according to claim 1 in which the olefin isomer component has a viscosity at 100° C. of 2 to 10 cS.

7. A well fluid according to claim 1 in which the olefin isomer component comprises a liquid olefin isomer component produced by the double bond isomerization of a waxy $C_{20}$–$C_{24}$ 1-olefin.

8. A well fluid according to claim 1 in which the olefin isomer component comprises a liquid olefin isomer component produced by the double bond isomerization of a waxy $C_{24}$–$C_{28}$ 1-olefin.

9. A well fluid according to claim 1 in which the amount of the olefin isomer component is from 5 to 80 weight percent of the blend.

10. A well fluid according to claim 1 in which the amount of the olefin isomer component is from 10 to 50 weight percent of the blend.

11. A well fluid according to claim 1 in which the paraffinic hydrocarbon component comprises a fraction in the $C_{12}$–$C_{14}$ range.

12. A well fluid according to claim 1 in which the paraffinic hydrocarbon component comprises a fraction in the $C_{14}$–$C_{18}$ range.

13. A well fluid according to claim 1 in which the paraffinic hydrocarbon component comprises a fraction in the $C_{16}$–$C_{32}$ range.

14. A well fluid according to claim 13 in which the low viscosity hydrocarbon comprises a hydrogenated dimer of a $C_8$ to $C_{16}$ olefin.

15. A well fluid according to claim 14 in which the hydrogenated dimer has a pour point not higher than −60° C., a viscosity of not more than about 3 cS (100° C.) and a flash point not below 120° C.

16. A well fluid according to claim 1 in which the olefinic hydrocarbon component comprises a 1-olefin in the $C_{12}$–$C_{16}$ range.

17. A well fluid according to claim 16 in which the olefinic hydrocarbon component comprises 1-tetradecene.

18. A well fluid according to claim 1 in which the olefinic hydrocarbon component comprises a dimer of a $C_8$–$C_{14}$ 1-olefin.

19. A well fluid according to claim 1 in which the olefinic hydrocarbon component comprises a $C_{16}$–$C_{32}$ olefin.

20. A well fluid according to claim 19 in which the olefinic hydrocarbon component comprises a $C_{16}$–$C_{32}$ olefin having a a pour point not higher than −60° C., a viscosity of not more than about 3 cS (100° C.) and a flash point not below 120° C.

21. In a well-drilling operation in which a well is drilled into a subterranean formation in a rotary drilling operation in which a well fluid is circulated down a drill string and returned to the surface, the improvement comprising the use of a well fluid of improved biodegradability and reduced marine toxicity as claimed in claim 1.

22. A well fluid which comprises a hydrocarbon oil comprising: (i) a liquid olefin isomer component produced by the double bond isomerization of a waxy $C_{20}$+ 1-olefin, and (ii) a low viscosity hydrocarbon which comprises at least one of a paraffinic hydrocarbon component of petroleum origin in the $C_{10}$–$C_{32}$ range, and an olefinic hydrocarbon component in the $C_{10}$–$C_{32}$ range, the oil having the following properties:

Viscosity at 100° C.; 0.5 to 4 cS

Viscosity at 40° C.; 0 to 30 cS

Pour point; not above +5° C.

Flash point; not less than 70° C., and wherein the proportions of the components, by weight, are:

olefin isomer component; 5 to 40 percent paraffinic hydrocarbon component; 50 to 90 percent olefinic hydrocarbon component; 5 to 40 percent.

23. A well fluid which comprises a hydrocarbon oil comprising: (i) a liquid olefin isomer component produced by the double bond isomerization of a waxy $C_{20}$+ 1-olefin, and (ii) a low viscosity hydrocarbon which comprises at least one of a paraffinic hydrocarbon component of petroleum origin in the $C_{10}$–$C_{32}$ range, and an olefinic hydrocarbon component in the $C_{10}$–$C_{32}$ range, the oil having the following properties:

Viscosity at 100° C. 0.5 to 4 cS

Viscosity at 40° C. 1.0 to 30 cS

Pour point not above +5° C.

Flash point not less than 70° C., and wherein the proportions of the components, by weight, are:

olefin isomer component 10 to 30 percent paraffinic hydrocarbon component 60 to 85 percent olefinic hydrocarbon component 10 to 30 percent.

* * * * *